(12) United States Patent
Elist

(10) Patent No.: US 12,036,123 B2
(45) Date of Patent: Jul. 16, 2024

(54) TESTICULAR IMPLANT DEVICE AND METHOD

(71) Applicant: Menova International, Inc., Beverly Hills, CA (US)

(72) Inventor: James J. Elist, Beverly Hills, CA (US)

( * ) Notice: Subject to any disclaimer, the term of this patent is extended or adjusted under 35 U.S.C. 154(b) by 249 days.

(21) Appl. No.: 17/172,506

(22) Filed: Feb. 10, 2021

(65) Prior Publication Data
US 2022/0249233 A1   Aug. 11, 2022

(51) Int. Cl.
*A61F 2/26* (2006.01)

(52) U.S. Cl.
CPC ........ *A61F 2/26* (2013.01); *A61F 2210/0076* (2013.01); *A61F 2220/0075* (2013.01); *A61F 2230/0071* (2013.01)

(58) Field of Classification Search
CPC ............ A61F 2/26; A61F 2/0059; A61F 2/02
See application file for complete search history.

(56) References Cited

U.S. PATENT DOCUMENTS

| | | | |
|---|---|---|---|
| 4,726,360 A | 2/1988 | Trick | |
| 5,445,594 A | 8/1995 | Elist | |
| 5,662,709 A * | 9/1997 | Elist | A61F 2/0059 600/38 |
| 5,669,870 A | 9/1997 | Elist | |
| 5,868,140 A * | 2/1999 | Miller | A61D 1/06 128/898 |
| 5,899,849 A | 5/1999 | Elist | |
| 6,475,137 B1 | 11/2002 | Elist | |
| 6,537,204 B1 | 3/2003 | Elist | |
| 8,986,193 B1 | 3/2015 | Elist | |
| 9,504,573 B1 | 11/2016 | Elist | |
| 9,839,718 B1 * | 12/2017 | Carrion | A61L 27/025 |
| 10,350,070 B2 | 7/2019 | Elist | |
| 2002/0091448 A1 * | 7/2002 | Atala | A61L 27/3817 623/23.71 |
| 2006/0282164 A1 * | 12/2006 | Seastrom | A61F 2/12 623/8 |
| 2008/0058955 A1 * | 3/2008 | Shirley | A61L 27/34 623/23.72 |

OTHER PUBLICATIONS

Steinbecker et al. Testicular Histology After Transparenchymal Fixation Using Polytetrefluoroethylene Suture: An Animal Model; Journel of Pediatric Surgery, vol. 34, Dec. 1999. (Year: 1999).*

* cited by examiner

*Primary Examiner* — Samuel G Gilbert
(74) *Attorney, Agent, or Firm* — Omni Legal Group; Omid E. Khalifeh; Ariana Santoro

(57) ABSTRACT

An implant device and method is provided. The implant may be a generally spherical, hollow body having one or more layers configured to be implanted within a scrotum and a cavity sized to receive a testis. Net sheeting provides structural rigidity to the implant and facilitates suturing of the implant to the patient. The cavity has a cavity configured to permit access to the cavity. Implantation involves administering one or more anesthetic agents to a patient having at least one testis and a scrotum; cutting an at least 1.5-inch longitudinal incision in the scrotum to expose the tunica vaginalis; cutting an at least 1.5-inch longitudinal incision in the tunica vaginalis; providing the testicular implant placing the testicular implant over the at least one testis; closing the at least 1.5-inch longitudinal incision in the tunica vaginalis; connecting the testicular implant to the tunica vaginalis; and closing the scrotum.

17 Claims, 4 Drawing Sheets

TESTICULAR IMPLANT DEVICE AND METHOD

GOVERNMENT CONTRACT

Not applicable.

CROSS-REFERENCE TO RELATED APPLICATIONS

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to surgically implanted devices and methods and, more particularly, to surgically implanted prostheses for the enhancement and enlargement of the appearance of the testicles and scrotum.

BACKGROUND

The anatomy of the male reproductive system generally comprises the penis and testicles. The penis acts as a conduit for urine to leave the body and also functions as the male sex organ. On the other hand, the testicles, also known as testes (and individually, a "testis"), are the glands where sperm and testosterone are produced. The scrotum, or scrotal sac, is a muscular sac that contains and protects the testicles, blood vessels and part of the spermatic cord. Moreover, the tunica vaginalis is a pouch of serous membrane covering the testes. The scrotum is located behind and underneath the penis.

Some individuals experience a small or unnatural looking scrotal area. For instance, individuals who use exogenous testosterone often experience a noticeable decrease in testicular size. Other conditions, including removal of one or both testicles due to cancer, testicular atrophy, undescended testicles, and originally smaller size of the testicles compared to the scrotal sac, may result in abnormally shaped or smaller than average scrotum size. In any event, a surgical correction of the aesthetic appearance of the scrotum may be required or desired. To that end, some testicular implants have attempted to correct this issue with limited success.

For instance, U.S. Pat. No. 5,662,709 teaches an implant device for improving the size and shape of a testis and configured to be implanted within a scrotum and attach to the testis. While this implant is well suited for male patients suffering from small gonad size or malformity, this device does not comprise one or more layers of net sheeting so as to add structure thereto. Thus, this teaching is deficient because it does not provide an implant of sufficient rigidity and which may be easily sutured to the patient's gonads.

Another attempt is seen with regard to U.S. Pat. No. 4,726,360, which teaches a penile prosthesis adapted for the treatment of erectile impotence. This disclosure provides an elongated flexible member for implantation within the corpus cavernosum of the penis and a pressure bulb configured to transfer fluid to the member. This teaching is also deficient because it fails to provide the natural appearance and feeling of the testicles, as provided by the present invention.

None of the aforementioned attempts comprise the advantages of the present invention. As such, there remains a need for a testicular implant for improving the size, symmetry, and appearance of the testes and/or scrotum.

SUMMARY

The present disclosure is directed to testicular implant devices that may expand the size of the scrotum and enhance overall scrotal appearance. More particularly, the testicular implant device may improve the appearance of the scrotal sac by providing symmetry to disproportionate testicles and increasing testicle size. Further, the testicular implant may appear natural in appearance and feeling to the unknowing observer.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

In accordance with one embodiment, the testicular implant may comprise a generally spherical, hollow body and a cavity. The generally spherical, hollow body may be configured to be implanted within a scrotum and thus, may be sized to be inserted into the scrotal sac via scrotal surgery. The cavity may be sized to receive a testis and may further comprise a cavity edge.

In some embodiments, the implant may be implantable within the scrotum having small testicles, that is, testicles which may be smaller than desired by the patient or those which are smaller than average. In such embodiments, the implant may serve to augment the testis without having any testicular function, such as hormone production. In alternate embodiments, the implant may be implantable within the scrotum having the testis which may be disproportionate in shape and/or size. In these embodiments, the implant may serve to symmetrize the existing testis. In still further embodiments, the implant may be implantable within the scrotum, wherein the scrotum may be pendulous or may comprise a large scrotal web. In such embodiments, the implant may serve to fill out the scrotum.

The spherical, hollow body may be formed so as to generally mimic the shape of a natural testis. In this manner, the body may expand the size of the scrotum. According to certain embodiments, the body may range between approximately 0.5 inches to 6 inches in diameter. In alternative embodiments, the body may be 6 inches or greater in diameter. A person of ordinary skill in the art will recognize the body may be formed in other shapes and sizes as well.

Moreover, the body may comprise one or more layers of net sheeting. The net sheeting may be stretchable and provide added structure to the implant. The net sheeting may be formed out of polypropylene, silicone, bovine tissue, marbles, strings, or other biocompatible material. In certain embodiments, the net sheeting may be laid out in a rectangular gird. The net sheeting may also facilitate suturing of the implant to the scrotum and/or the existing testis, as the case may be. In this manner, in some embodiments, the net sheeting may be disposed along the cavity edge, thereby spanning the inner circumference of the cavity.

The cavity may be concave and generally curve-shaped. In some embodiments, the cavity may comprise precisely enough space for the testis. In other embodiments, the cavity may be sized to receive the testis and also, provide additional space surrounding the testis. In still further embodiments where the testis has been removed or is otherwise smaller than normal, the cavity may comprise much less space.

As mentioned previously, the cavity may have the cavity edge. The cavity edge may serve as a means of ingress into the cavity. In this way, in embodiments where the testis may still be attached, the testis may fit through the cavity edge and into the cavity. Alternatively, the cavity edge (and therefore, the cavity) may encompass the spermatic cord or other portion of the scrotal sac.

In certain embodiments, the testicular implant may be formed out of a biocompatible material. As examples, the biocompatible material may comprise medical-grade silicone and/or medical-grade polyester. Alternatively, the testicular implant may be formed out of a gel-like material or may comprise saline, marbles, or other materials. In addition, the testicular implant may comprise one or more air pockets. Further, the testicular implant may be formed of one or more internal layers, which may provide rigidity. The testicular implant may feel soft and smooth along its surface area. In other embodiments, the testicular implant may feel textured along its surface area. Indeed, it is an objective of the present invention to provide a natural feeling and looking testicular implant.

In some embodiments, the testicular implant may comprise one or more functional layers. Any one of the one or more functional layers may be secured to the body, the cavity, and/or the cavity edge. While a number of functions performed or supported by the one or more functional layers are contemplated, the one or more functional layers may comprise antimicrobial, antibacterial, and/or antibiotic layers. In other embodiments, the one or more functional layers may be anti-adhesive, slick or lubricious layers, anti-inflammatory layers, controlled release layers, fluid reduction layers, or even a multifunctional combination of one or more of the foregoing.

Further, the implant may comprise an antibacterial, antimicrobial and/or antibiotic coating along either or both of an inner surface and an outer surface of the body. The antimicrobial, antibiotic and/or antibacterial coating may prevent infection from bacteria in or around the surgical site during or after implantation. Any antibacterial, antibiotic or antimicrobial coating known to those skilled in the art may be applied to the implant.

In one embodiment of the present invention, a method involving the aforementioned testicular implant device may be used to enhance to cosmetic appearance of the scrotum and the testes. The method may comprise the steps of: administering one or more anesthetic agents to a patient having at least one testis and a scrotum; cutting an at least 1.5-inch longitudinal incision in the scrotum to expose the tunica vaginalis; cutting an at least 1.5-inch longitudinal incision in the tunica vaginalis; providing a testicular implant having a generally spherical, hollow body and one or more layers of net sheeting; placing the testicular implant over the at least one testis; closing the at least 1.5-inch longitudinal incision in the tunica vaginalis; connecting the testicular implant to the tunica vaginalis; and closing the scrotum.

One or more of the above-disclosed embodiments, in addition to certain alternatives, are provided in further detail below with reference to the attached figures. The disclosed subject matter is not, however, limited to any particular embodiment disclosed.

Figure 1:
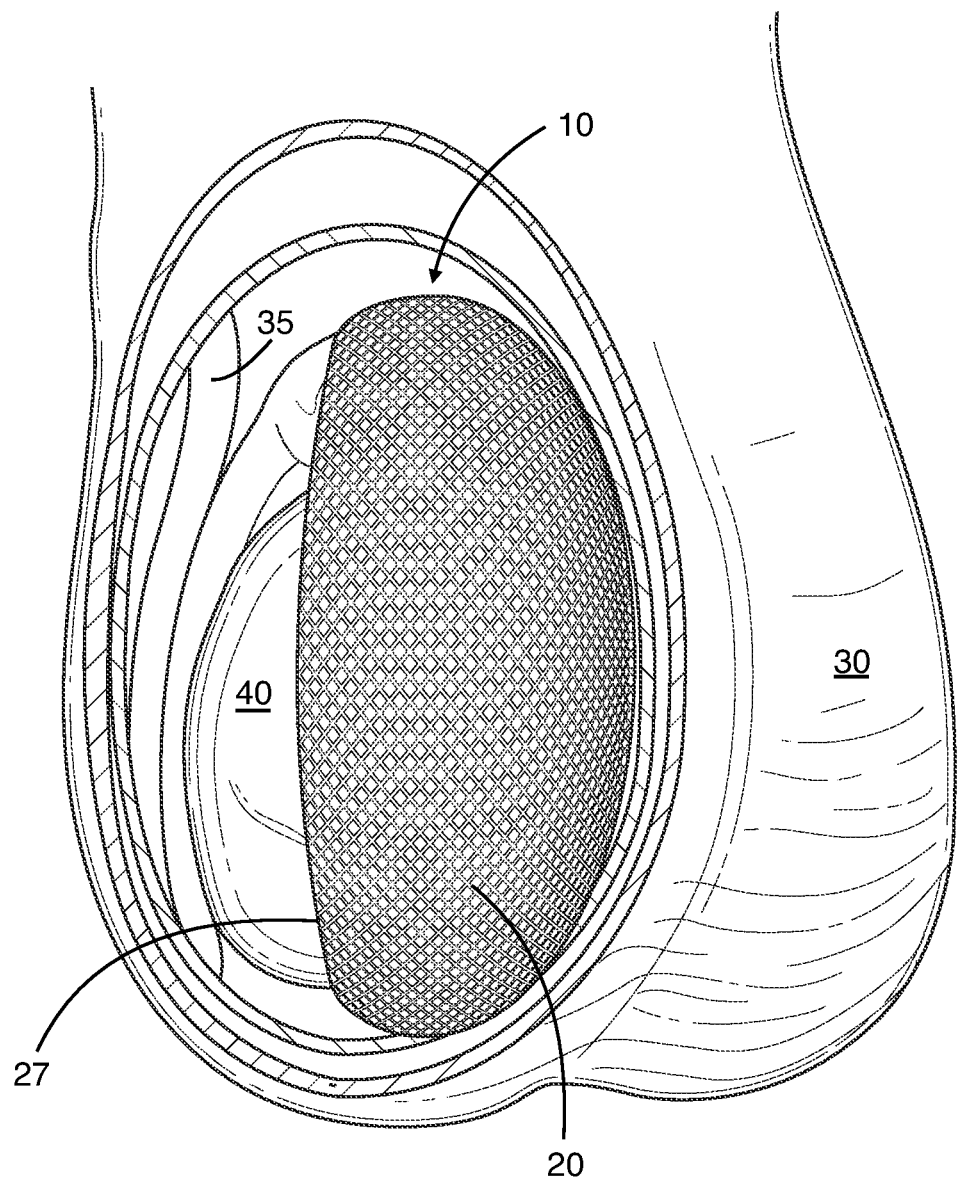
FIG. 1 shows a perspective view of an embodiment of the testicular implant device.

The disclosed embodiments may be better understood by referring to the figures in the attached drawings, as provided below. The attached figures are provided as non-limiting examples for providing an enabling description of the method and system claimed. Attention is called to the fact, however, that the appended drawings illustrate only typical embodiments of this invention and are therefore not to be considered as limiting of its scope. One skilled in the art will understand that the invention may be practiced without some of the details included in order to provide a thorough enabling description of such embodiments. Well-known structures and functions have not been shown or described in detail to avoid unnecessarily obscuring the description of the embodiments.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus The terms "couple," "coupled," "couples," "coupling," and the like should be broadly understood and refer to connecting two or more elements or signals, electrically, mechanically or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

DETAILED DESCRIPTION

Having summarized various aspects of the present disclosure, reference will now be made in detail to that which is illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims.

With reference to FIGS. 1-4, a testicular implant 10 is provided that, in some embodiments, may increase scrotal size while maintaining the natural look and feel thereof. In addition to increasing the apparent size of a patient's scrotum 30 and enhancing overall scrotal appearance, the implant 10 may also symmetrize the testes (individually, a testis 40). Further, the implant 10 may fill out the scrotal sac 30 for patients experiencing a pendulous scrotum or a large scrotal web. As another example, the implant 10 may be implanted where the patient naturally has undescended or small testicles. Further, the testicular implant 10 may improve a patient's self-confidence, self-esteem, and overall self-satisfaction.

As shown in FIG. 1, the testicular implant 10 may comprise a generally spherical, hollow body 20 and a cavity 25. The body 20 may be configured to be implanted within the scrotum 30. Accordingly, the body 20 may be sized so as to fit within the scrotal sac 30 as implanted during scrotal surgery. The body 20 may be attached to the scrotal sac 30 or the testis 40 using a biocompatible connecting agent. For instance, the biocompatible connecting agent may comprise sutures, adhesive, staples, or any other biocompatible material. As a whole, the implant 10 may not provide testicular function to the patient but instead, serves an aesthetic utility. In such embodiments, the body 20 may be slightly larger so as to sufficiently fill the scrotal sac 30 and provide a fuller, rounded appearance thereto.

The spherical, hollow body 20 may be cup-shaped and ovular. As such, the body 20 may be configured to be placed around the testis 40 or spermatic cord 35. Of course, as previously mentioned, the body 20 may also be secured to the scrotum 30. In certain embodiments, the body 20 may be configured so as to mimic the shape of the testis 40. By way of illustration, the body 20 may range between approximately 0.5 inches and 6 inches in diameter. Alternatively, the body 20 may be 6 inches or greater in diameter. Overall, the body 20 may be bigger or smaller depending on the patient's size and preferences. Moreover, in some embodiments, the body 20 may be custom molded for the patient in accordance with selected physical dimensions.

Figure 3:
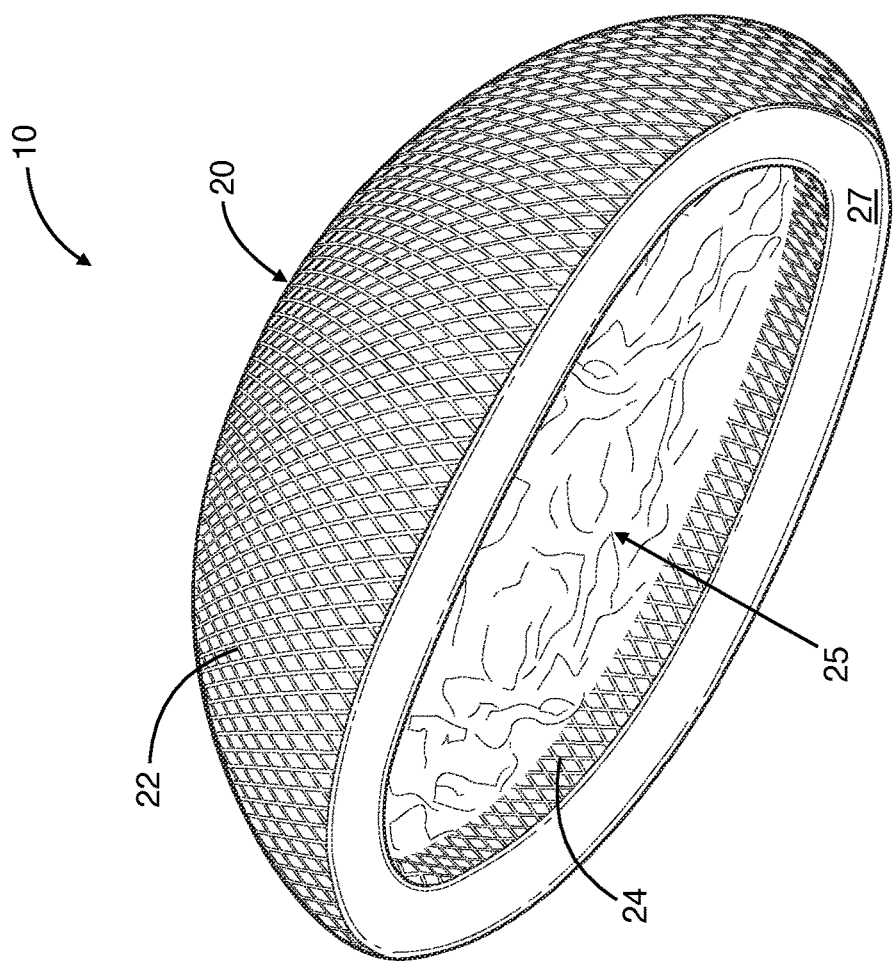
FIG. 3 shows a perspective view of an embodiment of the testicular implant device.
Figure 2:
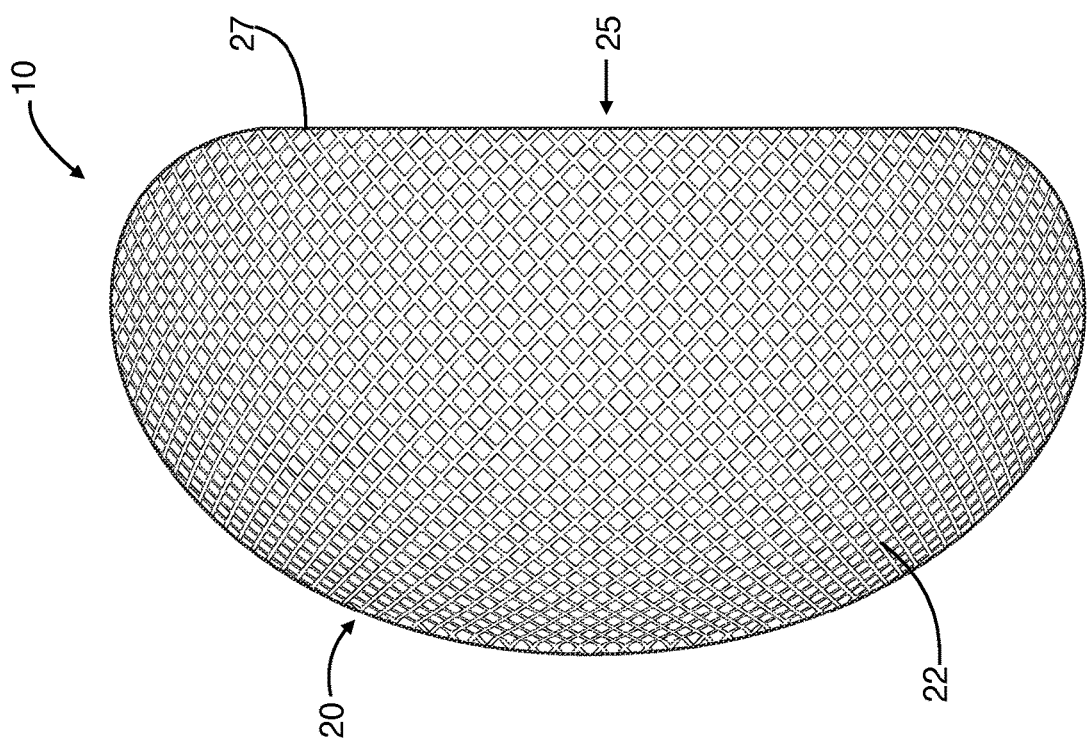
FIG. 2 shows a side view of an embodiment of the testicular implant device.
Figure 4:
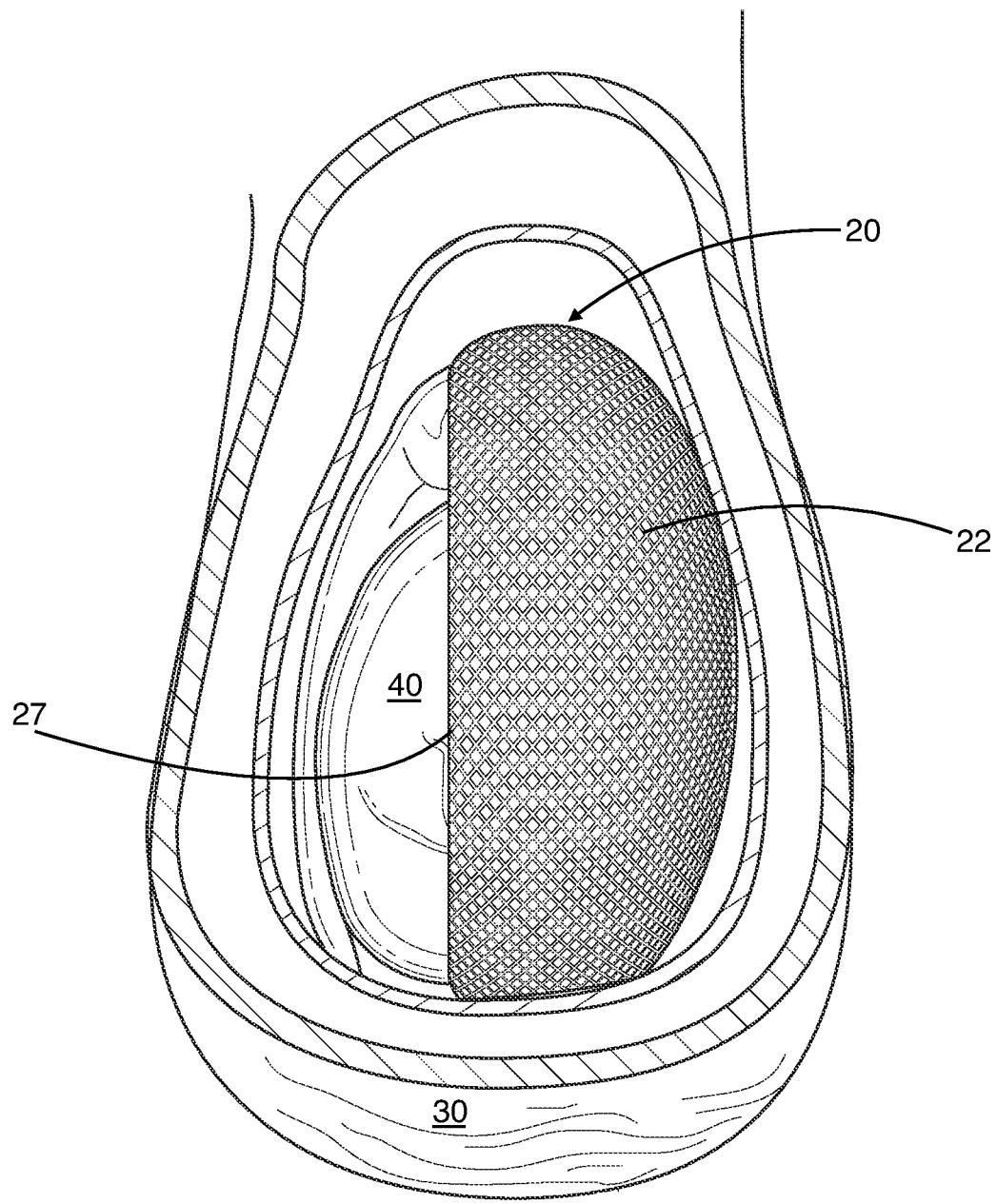
FIG. 4 shows a cross-section view of an embodiment of the testicular implant device.

As shown with greater detail in FIGS. 2-3, body 20 may also comprise one or more layers of net sheeting 22. It should be noted that, in some embodiments, the net sheeting 22 may not be visible from an outer surface of the body 20. In such embodiments, the one or more layers of net sheeting 22 may be imbedded within an inner surface (obscured from view) of the body 20. As shown and described herein, the one or more layers of net sheeting 22 may be imbedded within the outer surface of the body 20 and therefore, the net sheeting 22 may be visible from the outer surface of the body 20.

The one or more layers of net sheeting 22 may provide rigidity to the testicular implant 10 while also being stretchable. In accordance with certain embodiments, the one or more layers of net sheeting 22 may be formed out of polypropylene, silicone, bovine tissue, marbles, or strings. One of ordinary skill in the art will appreciate that the net sheeting 22 may be formed out of other medically-safe, biocompatible materials as well. In other embodiments, the net sheeting 22 may be formed out of non-biocompatible materials.

The net sheeting 22 may be formed of cross-hatched filaments, that is, filaments laid out in a rectangular grid. In other embodiments, the net sheeting 22 may be formed out of other geometric patterns or even, non-geometric patterns. In embodiments where the implant 10 may comprise more than one layer of net sheeting 22, each layer may be placed along the body 20 in opposing spaced-apart configurations so as to not steering the implant 10 in either lateral direction. In certain embodiments, the net sheeting 22 may comprise filaments having approximately ⅟32 inch thickness and ⅟32 inch spacing. In this manner, the net sheeting 22 may also facilitate suturing of the implant 10 to the testis 40, the spermatic cord 35, or elsewhere along the scrotum 30.

With reference to FIG. 3, the one or more layers of net sheeting 22 may comprise a mesh ring 24. The mesh ring 24 may be disposed along the cavity edge 27. Stated differently, the mesh ring 24 may extend along the inner circumference of the cavity 25. In such embodiments, the mesh ring 24 may align and surround the testis 40 and may facilitate suturing of the implant 10 to the testis 40.

With attention to any of FIGS. 1-4, the cavity 25 may comprise a cavity edge 27. The cavity edge 27 may define an opening of the cavity 25 and therefore, a means of ingress into the cavity 25. The body 20 may be secured to the testis 40, scrotum 30, spermatic cord 35 or elsewhere via the cavity edge 27. Specifically, the body 20 may be attached, such as by using the biocompatible connecting agent, to the patient along the cavity edge 25. In some embodiments, the entirety of the cavity edge 27 may be attached to the patient. In other embodiments, only a part of the cavity edge 27 may be attached to the patient.

Because the body 20 may be cup-shaped, the cavity 25 be correspondingly be curved and concave. In some embodiments, the cavity 25 may be sized to receive the testis 40. According to certain of those embodiments, the cavity 25 may be sized to receive the testis 40 and provide additional space surrounding the testis 40. Alternatively, the cavity 25 may be sized so as to fill out the scrotal sac 30 and therefore, may provide precisely enough space for the testis 40.

The testicular implant 10 may be formed out of a soft, smooth, and flexible material. Alternatively, the implant 10 may be formed out of a textured material. In accordance with certain embodiments, the out of a biocompatible material. As an example, the implant 10 may be formed out of medical-grade silicone, medical-grade polyester, medical-grade polypropylene, or a combination of the foregoing. One of ordinary skill in the art will appreciate that the testicular implant 10 may be formed out of other medically-safe, biocompatible materials as well.

According to further embodiments, the testicular implant 10 may comprise a gel-like material, saline, marbles, or other materials. In certain embodiments, the testicular implant 10 may be formed of one or more internal layers. Further, the one or more internal layers may comprise one or more air pockets. In other embodiments, the implant 10 may comprise a stretchable material. Overall, it is an object of the present invention to provide an implant 10 which is natural in look and feel.

In certain embodiments, the implant 10 may be formed of one or more functional layers. A number of exemplary, but not limited, functions performed or supported by the one or more functional layers are contemplated. For instance, in some embodiments, the one or more functional layers may be antimicrobial, antibacterial, and/or antibiotic layers. Such layers may comprise an antibiotic solution, or even one or more chemical elements or agents known to those skilled in the art as operative to kill microorganisms and/or stop their growth such as silver, copper, zinc, and ferric ammonium coatings, among others. In some embodiments, the one or more functional layers may be anti-adhesive. In such cases the one or more functional layers may comprise a hydrophilic coating which will be known to those skilled in the art. In some embodiments, the one or more functional layers may be slick or lubricious layers comprising a silicone coating. In some embodiments, the one or more functional layers may be anti-inflammatory layers comprising steroid coatings. In some embodiments, the one or more functional layers may be controlled release layers. In some embodiments, the one or more functional layers may be fluid reduction layers such as hydrogenated amorphous carbon coatings known to those skilled in the art.

It is even contemplated that in some embodiments, the one or more functional layers may comprise multifunctional coatings operative to perform a combination of the aforementioned exemplary functions, among others known to those skilled in the art. Likewise, one or more functions performed or supported by the one or more functional layers may be combined or otherwise stacked without departing from the invention. In some of these embodiments, the one or more functional layers may be embedded or impregnated within the implant 10. In other embodiments, the one or more functional layers may be secured to the body 20, the cavity 25, or the cavity edge 27 while the implant 10 is implanted within the patient's scrotum.

Further, the testicular implant 10 or one or more of the one or more layers of net sheeting 22 may be coated with one or more of an antibacterial coating, an antimicrobial coating, or an antibiotic coating (collectively referred to as the "coating"). The coating may reduce the risk of infection of the surgical site by immobilizing bacteria and providing continuous antimicrobial activity, thereby disallowing bacteria on the skin to infect the surgical site. Such coating may comprise iodine, active chlorine, concentrated alcohols, phenolic substances, cationic substances, oxidizers, heavy metals, strong acids, and alkalis.

Figure 5:
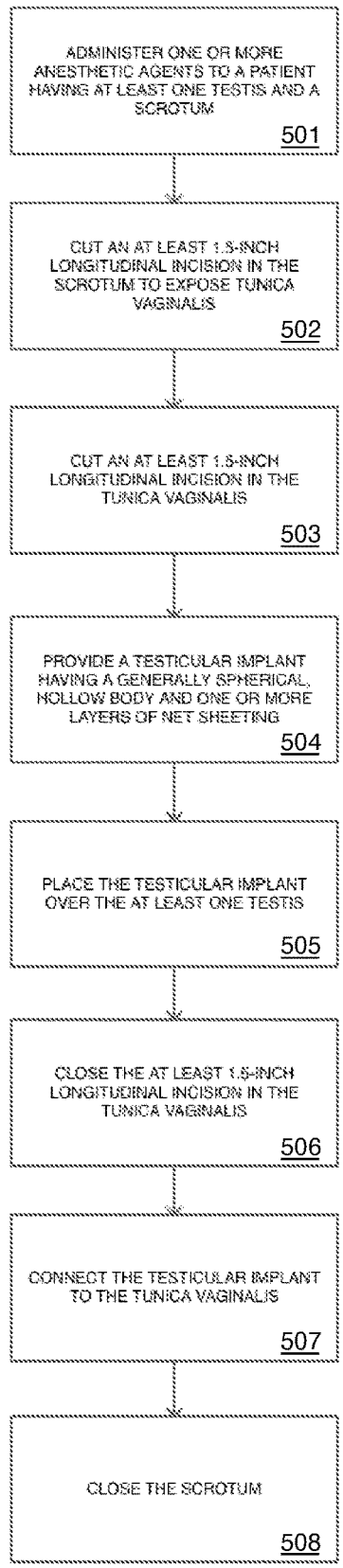
FIG. 5 shows an embodiment of the testicular implant method.

With reference to FIG. 5, one embodiment of the present invention may involve a method of implanting the aforementioned testicular implant device. FIG. 5 illustrates a flowchart of one embodiment of the method of this invention. This method may improve scrotal appearance by cosmetically correcting conditions such as small testicles, disproportionate scrotum, and other related diagnoses. In particular, the method may provide additional size to the testicles, thereby enhancing the size of the scrotum. Additionally, the method may symmetrize the testicles.

In certain embodiments, including that demonstrated in FIG. 5, the method may comprise the steps of: administering one or more anesthetic agents to a patient having at least one testis and a scrotum (block 501); cutting an at least 1.5-inch longitudinal incision in the scrotum to expose the tunica vaginalis (block 502); cutting an at least 1.5-inch longitudinal incision in the tunica vaginalis (block 503); providing a testicular implant having a generally spherical, hollow body and one or more layers of net sheeting (block 504); placing the testicular implant over the at least one testis (block 505); closing the at least 1.5-inch longitudinal incision in the tunica vaginalis (block 506); connecting the testicular implant to the tunica vaginalis (block 507); and closing the scrotum (block 508).

Initially, the one or more anesthetic agents may be administered (block 501). The one or more anesthetic agents may render the patient unconscious or otherwise alter or reduce the patient's conscious state, sensation and perception of pain resulting from the procedure. In some embodiments, the one or more anesthetic agents may comprise general anesthesia or spinal anesthesia. In further embodiments, the one or more anesthetic agents may comprise general twilight anesthesia. In these embodiments, the general anesthesia may be administered in a mild dose so as to cause mild sedation and anxiolysis. In other embodiments, the one or more anesthetic agents may comprise a local anesthetic agent. For instance, the one or more anesthetic agents may be injected around the scrotal area. In such embodiments, the one or more anesthetic agents may comprise the local anesthetic agent, such as lidocaine, other long-acting local anesthetic agents, or combinations thereof.

Once the one or more anesthetic agents have been administered (block 501), the at least 1.5-inch longitudinal incision may be cut in the scrotum (block 502). In so doing, the tunica vaginalis may be exposed. After the 1.5-inch incision has been cut (block 502), the testicular implant may be provided (block 504). In some embodiments, the testicular implant may be similar or identical to that described above with regard to the testicular implant device. Moreover, in certain embodiments, providing the testicular implant (block 504) may further comprise selecting an appropriately-sized testicular implant. For instance, the appropriately-sized testicular implant may be based on the patient's anatomy or desired outcome.

Next, the testicular implant may be placed over the at least one testis (block 505). The testicular implant may be placed over the at least one testis along the cavity edge of the implant, as described above. Stated differently, the cavity of the testicular implant may receive the at least one testis, thereby causing the cavity edge to abut the testis. In some embodiments, only a part of the cavity edge may abut and ultimately secure to the at least one testis. In other embodiments, the entirety of the cavity edge may abut and secure to the testis.

After the testicular implant has been placed over the at least one testis (block 505), the at least 1.5-inch longitudinal incision in the tunica vaginalis may be closed (block 506). According to certain embodiments, the 1.5-inch longitudinal incision may be closed using any biocompatible connecting agent. By way of example, the biocompatible connecting agent may comprise sutures, staples, or adhesive.

Similarly, the testicular implant may then be connected to the tunica vaginalis using a biocompatible connecting agent (block 507). In accordance with certain embodiments, the one or more layers of net sheeting may be sutured to the tunica vaginalis. Finally, the scrotum may be closed (block 508). In certain embodiments, the scrotum may likewise be closed using a biocompatible connecting agent. In some embodiments, the same biocompatible connecting agent may be used to close the 1.5-inch longitudinal incision in the tunica vaginalis (block 506), connect the testicular implant to the tunica vaginalis (block 507), and close the scrotum (block 508). In alternate embodiments, a different biocompatible connecting agent may be used.

In further embodiments, the testicular implant method may also comprise trimming the testicular implant to a desired form. The desired form may be based on the size of the at least one testis. In this manner, the desired form may accommodate the natural shape and size of the at least one testis. In some embodiments, the desired form may also be based on the desires of the patient.

In still further embodiments, the testicular implant method may further comprise irrigating with one or more antibiotic agents. In some embodiments, the one or more antibiotic agents may comprise a triple antibiotic solution with rifampicin. In alternate embodiments, the one or more antibiotics may comprise a triple antibiotic solution mixed with minocycline or a combination of rifampicin and minocycline. However, other antibiotics or antibiotic solutions may be applied in accordance with the method. Indeed, a person of ordinary skill in the art will recognize other such appropriate antibiotics. The one or more antibiotics may inhibit or slow the growth of bacteria in the surgical site.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

CONCLUSIONS, RAMIFICATIONS, AND SCOPE

While certain embodiments of the invention have been illustrated and described, various modifications are contemplated and can be made without departing from the spirit and scope of the invention. For example, the testicular implant device and method may be implanted if the patient has smaller than desired testicles or testicles that are disproportionate. Accordingly, it is intended that the invention not be limited, except as by the appended claims.

The teachings disclosed herein may be applied to other systems, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the testicular implant device and method with which that terminology is associated. In general, the terms used in the following claims should not be construed to limit the testicular implant device and method to the specific embodiments disclosed in the specification unless the above description section explicitly define such terms. Accordingly, the actual scope encompasses not only the disclosed embodiments, but also all equivalent ways of practicing or implementing the disclosed system, method and apparatus. The above description of embodiments of the testicular implant device and method is not intended to be exhaustive or limited to the precise form disclosed above or to a particular field of usage.

While specific embodiments of, and examples for, the method, system, and apparatus are described above for illustrative purposes, various equivalent modifications are possible for which those skilled in the relevant art will recognize.

While certain aspects of the method and system disclosed are presented below in particular claim forms, various aspects of the method, system, and apparatus are contemplated in any number of claim forms. Thus, the inventor reserves the right to add additional claims after filing the application to pursue such additional claim forms for other aspects of the testicular implant device and method.

What is claimed is:

1. A testicular implant, comprising:
a generally spherical, hollow body configured to be implanted within a scrotum and having one or more layers of net sheeting; and
a cavity sized to receive a testis and having a cavity edge; and
a mesh ring extending along an inner circumference of the cavity edge and configured to facilitate suturing of the testicular implant to the testis.

2. The testicular implant of claim 1, wherein the implant is formed of a biocompatible material.

3. The testicular implant of claim 1, wherein the implant is formed of a gel-like material, saline, marbles, or one or more internal layers formed of one or more of medical-grade silicone, polyester, and one or more air pockets.

4. The testicular implant of claim 1, wherein the one or more layers of net sheeting are formed of polypropylene, silicone, bovine tissue, or other biocompatible material.

5. The testicular implant of claim 1, wherein the body attaches is configured to attach within the scrotum using a biocompatible connecting agent.

6. The testicular implant of claim 1, wherein the one or more layers of net sheeting are configured to attach the body to the tunica vaginalis.

7. The testicular implant of claim 6, wherein the one or more layers of net sheeting are configured to attach the body to the tunica vaginalis using a biocompatible connecting agent.

8. The testicular implant of claim 7, wherein the biocompatible connecting agent is sutures.

9. The testicular implant of claim 1, wherein the one or more functional layers comprises one or more of antibiotic layers, antimicrobial layers, antibacterial layers, anti-adhesive layers, hydrophilic coating, lubricious layers, anti-inflammatory layers, controlled release layers, and fluid reduction layers.

10. The testicular implant of claim 1, wherein the body is at least 0.5 inches in diameter.

11. A testicular implant, comprising:
a generally spherical, hollow body configured to be implanted within a scrotum;
a cavity sized to receive a testis and having a cavity edge; and
a mesh ring extending along an inner circumference of the cavity edge and configured to facilitate suturing of the testicular implant to the testis;

wherein the body is configured to attach within the scrotum along the cavity edge using sutures.

12. A testicular implant method, comprising the steps of:

administering one or more anesthetic agents to a patient having at least one testis and a scrotum;

cutting an at least 1.5-inch longitudinal incision in the scrotum to expose tunica vaginalis; cutting an at least 1.5-inch longitudinal incision in the tunica vaginalis;

providing a testicular implant having (a) generally spherical, hollow body; (b) one or more layers of net sheeting; (c) a cavity sized to receive a testis and having a cavity edge; and (d) a mesh ring extending along an inner circumference of the cavity edge and configured to facilitate suturing of the testicular implant to the testis;

placing the testicular implant over the at least one testis;

closing the at least 1.5-inch longitudinal incision in the tunica vaginalis;

connecting the testicular implant to the tunica vaginalis; and closing the scrotum.

13. The testicular method of claim 12, further comprising irrigating with one or more antibiotic agents.

14. The testicular implant method of claim 12, further comprising trimming the testicular implant to a desired form, wherein the desired form is based on the size of the at least one testis.

15. The testicular implant method of claim 12, wherein placing the testicular implant over the at least one testis further comprises placing the cavity over the at least one testis.

16. The testicular implant method of claim 12, wherein connecting the testicular implant to the tunica vaginalis further comprises suturing the testicular implant to the tunica vaginalis.

17. The testicular implant method of claim 16, wherein suturing the testicular implant to the tunica vaginalis further comprises suturing the one or more layers of net sheeting to the tunica vaginalis.

* * * * *